United States Patent
Hashmi et al.

(10) Patent No.: US 7,612,193 B2
(45) Date of Patent: Nov. 3, 2009

(54) PRIMERS FOR EXONS OF VARIANTS OF RHCE AND RHD GENES

(75) Inventors: Ghazala Hashmi, Holmdel, NJ (US); Michael Seul, Fanwood, NJ (US); Marion E. Reid, Jamaica Estates, NY (US); Michael Pierce, Flemington, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 0 days.

(21) Appl. No.: 12/206,859

(22) Filed: Sep. 9, 2008

(65) Prior Publication Data

US 2009/0054636 A1    Feb. 26, 2009

Related U.S. Application Data

(62) Division of application No. 11/257,285, filed on Oct. 24, 2005, now Pat. No. 7,449,295.

(60) Provisional application No. 60/621,196, filed on Oct. 22, 2004.

(51) Int. Cl.
*C07H 21/04* (2006.01)
*C12N 15/12* (2006.01)

(52) U.S. Cl. .................................................. 536/24.33
(58) Field of Classification Search ....................... None
See application file for complete search history.

(56) References Cited

U.S. PATENT DOCUMENTS 7,449,295 B2 * 11/2008 Hashmi et al. ................. 435/6

* cited by examiner

*Primary Examiner*—James Martinell
(74) *Attorney, Agent, or Firm*—Eric P. Mirabel

(57) ABSTRACT

Disclosed are a method and an algorithm for genetic cross-matching based on the comparison of recipient and donor genotypes—and the underlying combinations of alleles and haplotypes. The method of the invention, rather than focusing on phenotype prediction, instead relies on a comparison of genetic variants identified in the recipient and available donors, whose information preferably will be compiled in a widely available donor registry, to maximize molecular compatibility. The genotypes can be matched based on the weighted clinical significance of a genotypic difference between donor and recipient, such that certain mismatches are more acceptable than others.

1 Claim, 2 Drawing Sheets

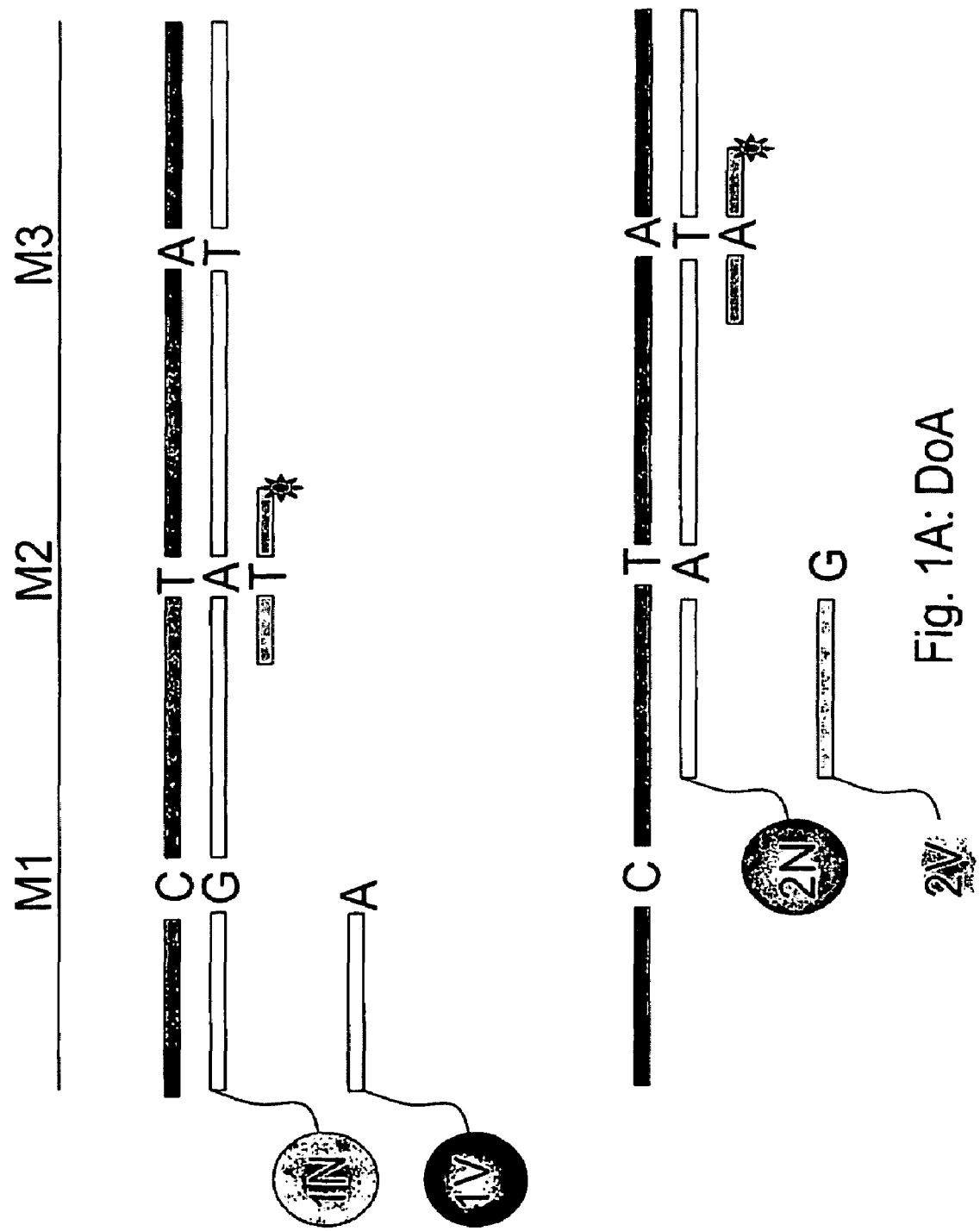
Fig. 1A: DoA

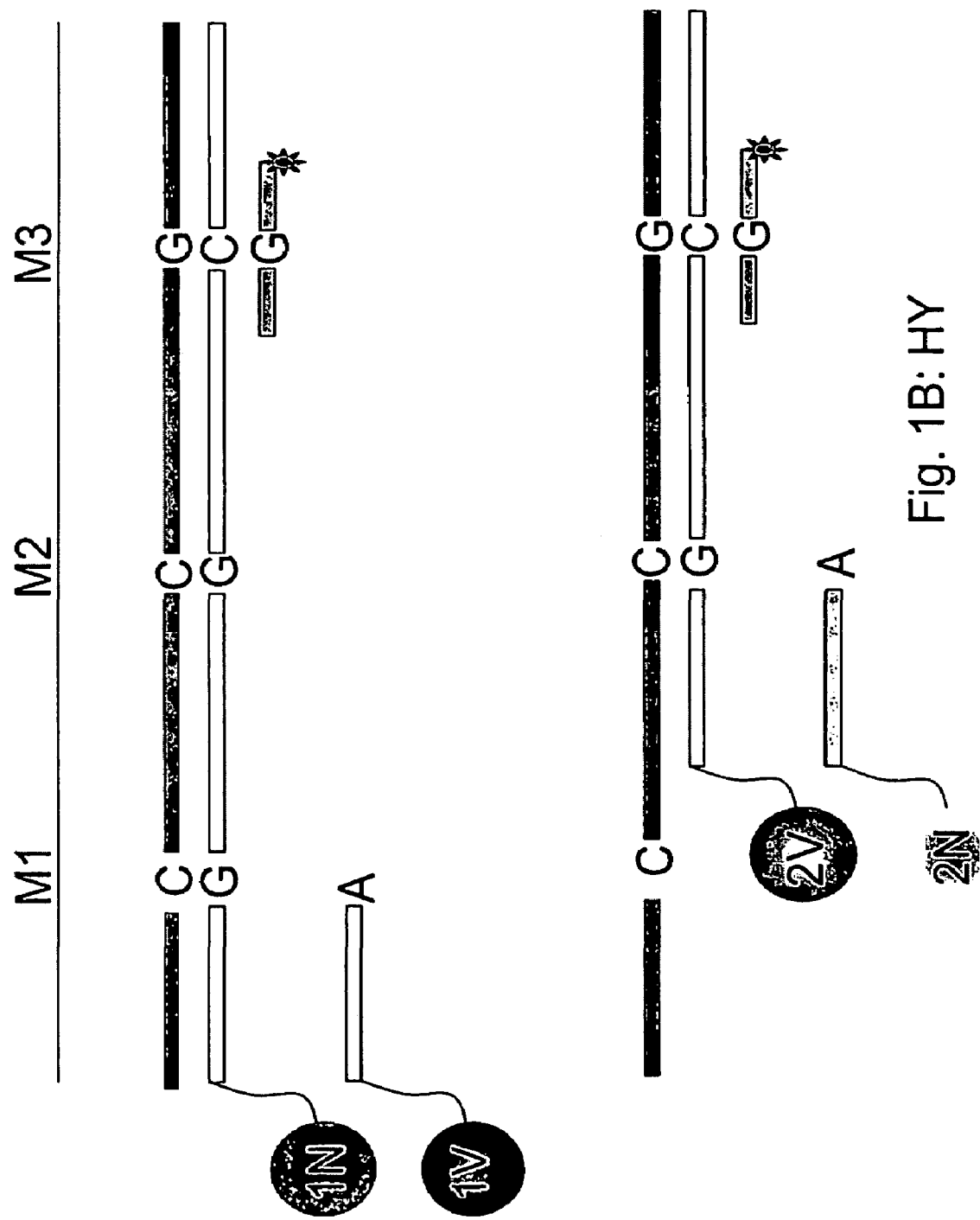
Fig. 1B: HY

US 7,612,193 B2

PRIMERS FOR EXONS OF VARIANTS OF RHCE AND RHD GENES

RELATED APPLICATIONS

This application is a divisional of U.S. application Ser. No. 11/257285, filed Oct. 24, 2005 now U.S. Pat. No. 7,449,295, which claims priority to Provisional Application 60/621,196, filed Oct. 22, 2004.

BACKGROUND

The identification of antibodies and the provision of antigen-negative blood forms the basis for safe blood transfusion by minimizing the risk of adverse transfusion reactions, triggered when antibodies circulating in the patient's blood stream encounter antigens displayed on a donor's erythrocytes. Current practice in transfusion medicine provides for the serological typing and labeling of all donor blood for ABO and RHD antigens to facilitate the matching of red blood cell components to the recipient's blood type. The further reduction of allo-immunization remains an important clinical concern, and therefore it would be highly desirable to match additional blood group antigens. However, this practice is precluded by the lack of appropriate antisera, and the complexity of labor-intensive serological typing protocols, particularly when encountering multiple allo-antibodies. As a result, most donor centers screen only a selected cohort of donors and maintain limited inventory of antigen-negative units. This practice can introduce delays in treatment and thus create significant additional expense in patient care, and also can exacerbate emergency situations.

Comprehensive donor DNA typing of donors, as recently described (see Reid et al.; Transfusion May 2005) will enable donor centers to maintain a registry of prospective donors, and large and diverse inventories of fully characterized blood products available for instant shipping. In addition, the analysis of blood group genes at the DNA level provides a detailed picture of the allelic diversity that underlies phenotypic variability, an approach which helps in addressing clinical problems that cannot be addressed by serological techniques, such as determination of antigen types for which the available antibodies are weakly reactive, the analysis of recently transfused patients, or the identification of fetuses at risk for hemolytic disease of the newborn. Although the genotype may not reflect the phenotype, DNA analysis will identify the potential antigen-negative which, if desirable, can be confirmed by classical hemagglutination. Comprehensive DNA typing also can be extended to recipients and indeed can be applied population-wide by invoking practical methodologies, preferably eMAP™, performed on a BeadChip™ platform (See U.S. application Ser. No. 10/271,602, incorporated herein by reference).

Genetic Cross-Matching

A match, or near-match, between selected marker identified in a recipient, and in candidate donors of transfused blood—the markers corresponding to polymorphic sites located in genes encoding blood group antigens and specifically including minor blood group antigens—generally will minimize the risk of recipient immunization and, in immunized recipients, the risk of alloantibody-mediated adverse immune reactions following transfusion. That is, if the set of markers is selected to probe the relevant alleles associated with clinically significant hemolytic transfusion reactions ("allo-reactions"), then a comparison of markers of recipient and donor will permit the selection of donors that are genetically compatible with a given recipient. For example, each of a set of monozygotic twins, genetically identical, would be the ideal donor for the other. In the case of transfusion, the requirement of genetic identity—or near-identity—of recipient and candidate donor is limited to a set of relevant genes which—when expressed—encode certain human erythrocyte antigens (HEA) displayed on blood-borne cells against which the recipient either already has made (on the basis of earlier exposure) antibodies ("allo-antibodies") or can make antibodies. Thus, markers correlating with human erythrocyte antigens (HEA) including the "major" antigens (A, B and Rh) as well as a number of clinically relevant "minor" antigens (e.g., Duffy, Kell, Kidd, M N S, Dombrock and others), as discussed in U.S. application Ser. No. 11/168224, are of interest.

The benefit of such a genetic cross-matching procedure will be to minimize or reduce not only the risk of adverse immune reactions, but also the risk of immunizing recipients in the first place, to eliminate the need for and to enable the rapid selection of blood products for transfusion from a group of registered and fully characterized donors, also referred to herein as a donor registry. Once fully implemented, genetic implemented, genetic cross-matching will eliminate the narrowing bottleneck created by the increasing cost of serological reagents and complex and labor-intensive protocols as well as the need for repeat testing.

SUMMARY

Disclosed are a method and an algorithm for genetic cross-matching based on the comparison of recipient and donor genotypes—and the underlying combinations of alleles and haplotypes. Preferably, as described, in a co-pending application, entitled "Multiplexed Analysis of Polymorphic Loci by Concurrent Interrogation and Enzyme-Mediated Detection," filed Oct. 15, 2002, Ser. No. 10/271,602 (incorporated by reference), genotypes are determined in a single ("multiplexed") test to permit rapid, large-scale typing. The method of the invention, rather than focusing on phenotype prediction as advocated in conventional procedures, instead relies on a comparison of genetic variants identified in the recipient and available donors, whose information preferably will be compiled in a widely available donor registry, to maximize molecular compatibility. Using, for example, a BeadChip™ format such as disclosed herein, to enable, at reasonable cost, large-scale comprehensive genotyping of clinically relevant transfusion antigens, preferably performed in a neonatal screening context, would permit the transfusion antigen genotype ("TAG")—and related genetic information—to become part of individual medical records which could be stored in a readily accessible format such as implantable chips, or other electronic tags carried, for example, in bracelets.

BRIEF DESCRIPTION OF THE FIGURES

FIGS. 1A and 1B illustrates use of multiple encoded probes to resolve ambiguity through phasing.

DETAILED DESCRIPTION

For present purposes, we define a genotype as a string of markers at selected polymorphic sites (also referred to herein as alleles); that is, values giving the configuration of target nucleic acid markers located within one or more genes of interest. Preferably, each designated site is interrogated with a pair of elongation probes of which one is designed to detect the normal (N) allele, the other to detect a specific variant (V) allele, under conditions ensuring that polymerase-catalyzed probe elongation occurs for matched probes, that is those matched to the allele at the 3'-terminus, but not for mismatched probes. The pattern of assay signal intensities representing the yield of individual probe elongation reactions in accordance with this eMAP™ format (see Ser. No. 10/271,602, supra), is converted to a discrete reaction pattern—by application of preset thresholds—to ratios (or other combinations) of assay signal intensities associated with probes within a pair of probes directed against each marker.

A genotype then is represented by a string, $G=\{(NV)_{ik}\}$ where i enumerates the genes in the set of selected genes of interest, and k enumerates designated polymorphic sites within the i-th gene, and where the pair (NV) can assume values of AA, AB (or BA) and BB. In a preferred embodiment, the signal intensities associated with a pair of probes directed to the same marker, preferably corrected by removing non-specific ("background") contributions, and one such intensity, $i_N$, representing the amount of normal allele, and the other such intensity, $i_V$, representing the amount of variant allele in the sample, are combined to form the discrimination parameter $\Delta=(i_N-i_V)/(i_N+i_V)$, a quantity which varies between $-1$ and $1$. For a given sample, a value of $\Delta$ below a preset lower threshold indicates a call of homozygous normal, a value of $\Delta$ above a preset upper threshold indicates a call of homozygous variant, and a value of $\Delta$ above the lower and below the upper threshold indicates a call of heterozygous. A transfusion antigen genotype is represented by a string, $G=\{\Delta_{ik}\}$, where, as before, i enumerates the genes in the set of selected genes of interest, and k enumerates designated polymorphic markers within the i-th gene. Accordingly, a transfusion antigen genotype is designated herein either in the representation AA, AB (or BA) and BB or, equivalently, in the representation 1, 0, $-1$.

Assigning Alleles: Decomposition of Genotypes into Haplotypes—Expressed antigenic determinants reflect the specific allelic combinations of the encoding genes. A genotype generally represents a combination of two constituent haplotype strings, here denoted H1 and H2, each in the form of a ternary string such that H1 OR H2 generates the genotype. All compatible 2-string combinations are determined in a process also referred to herein as allele assignment or automated allele analysis ("AAA"), preferably performed automatically, using a program such as the AAA program for Automated Allele Analysis, elaborated in co-pending application, entitled: "Automated Analysis of Multiplexed Probe Target Interaction Patterns: Pattern Matching and Allele Identification," filed Aug. 2, 2004, Ser, No. 10/909,638 (incorporated by reference).

This application also discloses a method of "error correction" wherein a reaction pattern (of probes-targets) generated from an assay is compared, digit by digit, to the possible reaction patterns, that is, strings representing 2-allele combinations of known alleles; a list of such reference strings is also referred to herein as a hit table. For digits which do not match, the error correction is by way of changing individual digits in the string as judged necessary in order to produce a match with a valid reference string (generated from known allele combinations).

Several allele or haplotype combinations generally may be compatible with a single genotype, as illustrated in an Example below, and this issue is addressed herein by an application of the "phasing" methodology previously disclosed in Ser. No. 10/271,602, supra.

Donor Registry—Assuming, without loss of generality, application of the preferred embodiment of multiplex genotype determination, genotypes of prospective donors are determined in accordance with the eMAP format. In a preferred embodiment, the genotype, and the set of constituent allele or haplotype combinations, are stored in form of a list of records, in an appropriate database format, such as MicroSoft Access or SQL, as follows:

$\{G=\{(N,V)_{ik}\}; \{\text{Haplotype Combinations}\}; 1 \leq I \leq \Gamma; 1 \leq k \leq M(i); p\}$, or $\{G=\{\Delta_{ik}\}; \{\text{Haplotype Combinations}\}; 1 \leq 23 \ \Gamma; 1 \leq k \leq M(i); p\}$, where $\Gamma$ denotes the number of selected genes, such as those encoding blood group antigens, M(i) denotes the number of markers in the i-th gene and p denotes the address ("pointer") associated with a memory location, for example in a database such as an inventory, containing a list of donors of given genotype. Within the inventory, compatible donors may be sorted by additional criteria such as date of sample collection, completeness of characterization (e.g., knowledge of additional antigen types such as HLA or HPA), age, gender, etc.

Selection Designated Polymorphic Sites and Table of Associated Weights—A mismatch between patient and donor alleles or haplotypes can lead to immunization, or to adverse immune reactions of differing severity, mediated by antibodies circulating within the patient's serum recognizing expressed epitopes that are encoded by donor marker alleles (or antigenic determinants). To represent this degree of significance; the invention introduces a set of numerical weights, $w_{ik}$, associated with the k-th designated marker on the i-th gene of interest. The relative magnitude of these weights reflects the severity of known or anticipated transfusion reactions associated with a mismatch at the corresponding site, and the allo-reaction(s) associated with a mismatch of the corresponding phenotypes. As illustrated in Tables 1 and 2, weights may be chosen to reflect empirical measures of clinical significance such as NONE (0), MILD (1), MILD-TO-SEVERE (3), SEVERE (5). Silencing mutations producing a null phenotype in the donor generally will enhance compatibility given the absence of the corresponding antigen. If allo-antibodies have been identified, the corresponding cognate antigen and associated markers are given a high weight, reflecting the clinical significance of the antibody, as shown in Table 4.

Matching Alleles of Genotypically Identical Recipient and Donor: Dombrock

This example uses three markers in the Dombrock system, associated with $Do^a/Do^b$, namely: $M_1$ (378 C>T); $M_2$ (624 T>C); $M_3$ (793 A>G) to illustrate the matching of a genotypically identical recipient and prospective donor.

A reaction pattern representing the interaction of a set of probe pairs and target (where one probe in a pair can indicate the presence of a "normal" allele, and the other probe in the pair indicates the presence of a "variant" allele) can be generated using, e.g., the eMAP assay format with a set of probe pairs capable of annealing to Dombrock genes (or amplicons or targets derived from Dombrock genes by PCR amplification or otherwise). For the three selected markers, a possible reaction pattern is: AB AB AB, that is a reaction pattern: 0, 0, 0. In a diploid genome, a particular reaction pattern corresponds to a combination of at least two alleles. Thus, this reaction pattern is first decomposed into the patterns repre sented by combinations of alleles, in this case either of the following (see Table 4):

AB AB AB=AAA OR BBB; that is DoA or DoB alternatively:

AB BA AB=AB BA BA=ABB OR BAA; that is Hy or Jo where "A" designates a normal allele and "B" designates the variant. Next, a "mismatch matrix" is constructed which indicates by application of weights, the severity of adverse clinical outcomes resulting from a mismatch. In the present case:

|     | AAA | BBB | BAA | ABB |
|-----|-----|-----|-----|-----|
| AAA | 0   | $w_3$ | $w_2$ | $w_2 + w_3$ |
| BBB |     | 0   | $w_2 + w_3$ | $w_2$ |
| BAA |     |     | 0   | $w_3$ |
| ABB |     |     |     | 0   |

Where weighting is applied to a mismatch in the allele (of the gene of interest, here Dombrock). These weights, preferably in a separate look-up table, might be, w1=1,w2=5, w3=5 (or other preset values, that are informed by empirical knowledge relating to clinical significance).

Resolving Allelic Ambiguities by "Phasing"

Multiple biallelic combinations may be compatible with a specific genotype determined over a set of selected markers. Matching of a recipient with a known genotype, GR, to a compatible donor of the same genotype requires matching of the actual underlying set of alleles (or haplotypes). These can be established by the following phasing strategy which establishes 2-point correlations (see also US Publication No. 20040002073A1, incorporated by reference). The strategy entails probing of bead-displayed elongation products using tagged hybridization probes, either one at a time (in multiple rounds of annealing and deannealing) or in a parallel process, preferably involving multiple colors of detection, where preferably in such a case, the elongation product itself is not labeled.

This is illustrated in FIGS. 1A and 1B, where markers M1, M2 and M3 (with polymorphic sites which can be C, T or A, respectively, as in the first allele (corresponding to DoA), or C, C, G, respectively, as in the second allele (corresponding to Hy), or other nucleotides) are interrogated using tagged probes. Differentially labeled extendable probes are used for detection of a first allele, where probe "1N" (directed to marker M1) has a "G" nucleotide at the 3' terminus, probe "1V" (also directed to marker M1) has an a "A" nucleotide at the 3' terminus, probe "2N" (directed to marker M2) has an "A" nucleotide at the 3' terminus, probe "2V" (also directed to marker M2) has a "G" nucleotide at the 3' terminus. Depending on the M1, M2 and M3 marker combinations, different combinations of the probes are elongated, generating different signal intensity patterns as interaction products interact with tagged probes, as shown in FIGS. 1A and 1B. Thus, if DoA is encountered (FIG. 1A), probe 1N is elongated, and decorated by a fluorescent probe annealing to the elongation product at the position of marker M2; conversely, if Hy is encountered (FIG. 1B), probe 2V is elongated, and decorated by a fluorescent probe annealing to the elongation product at the position of marker M3. The signal intensity pattern produced by addition of fluoresceinated probes (directed to markers M2 and/or M3, as shown) identifies either DoA and thus DoA OR DoB as the combination represented by the reaction pattern 0, 0, 0, or identifies Hy and thus Hy OR Jo as the combination represented by the reaction pattern 0,0,0. That is, phasing resolves the ambiguity.

Genetic Cross Matching: Distance between Haplotypes—Given a recipient genotype, preferably in the representation representing at least a substring of available donor genotypes (of one or more donors of identical genotype to the recipient), they are identified by haplotype (string) matching. Here, the recipient haplotype preferably comprises at least the set of marker alleles represented in the corresponding haplotype of available donors. In one embodiment, each of the strings, $H_2$, $H_R$ is compared to the set of strings, $\{H\}$, in a donor database, and matches are ranked in the order of an increasing weighted Hamming distance where the weights are preset so as to reflect clinical severity, as discussed in connection with the discussion of the mismatch matrix. For example, assuming there to be M mismatched alleles, a possible distance function is: $\Pi^2 = (1/M)3_{mismatched\ alleles}\ w^2$ Implementation—Preferably, a computer program implementing a string matching algorithm is used to perform the genetic cross matching automatically, to list available donor in the order of increasing $\Pi^2$ (or equivalent distance function) up to a maximal distance between patient and donor strings.

The pseudocode below summarizes the string matching algorithm (the terms "allele" and "haplotype" are used interchangeably). To optimize execution speed in handling the large data bases of interest, the implementation, such as that within wAAA™ (U.S. Ser. No. 10/909,638, supra), employs suitable data structures and invokes integer arithmetic.

```
SelectCompatibleDonors(DonorRegistry, RecipientHaplotypes);
{
    AssignAlleles(RecipientHaplotypes, DonorHaplotypes);
}
AssignAlleles(AlleleArray1, AlleleAray2, ReactionStr, hitTable);
{
    /*
    ** for each allele in hit table, determine mismatch with reaction pattern of
    ** interest, Allele0 is the first allele entry in hit table AlleleN is the last allele
    ** entry in hit table
    */
    minMismatch = 30;                        /* initiate to large number
                                                */
    FOR (A1=Allele0; A1≦AlleleN; A1++)
    {
        A1Hit = getHitStr(A1, hitTable);     /* retrieve from hit table
                                                string representing allele
                                                A1 */
        FOR (A2=A1; A2≦AlleleN; A2++)
```

-continued

```
    {
        A2Hit = getHitStr(A2, hitTable);
        combStr = OR(A1Hit, A2Hit);    /* construct allele
                                          combination by applying
                                          OR operation */
/*
** evaluate degree of mismatch between hitStr and reactionStr;
** speed up: if mismatch exceeds minMismatch + 2, quit loop
*/
        nMismatch = Compare(combStr, reactionStr, minMismatch);
        if(nMismatch < minMismatch)
        {
            minMismatch = nMismatch;
                                        /*clear old result */
            clearResult(AlleleArray1, AlleleArray2);
        }
                                        /*store new result */
        writeResult (A1, A2, AlleleArray1, AlleleArray2);
    }
}
/*
** post process result:
** count number of changed digits, make group call, sort candidate
assignments, etc.
*/
    PostProcessAlleleResult(AlleleArray1, AlleleArray2);
}
/* Genetic CrossMatching */
main( )
{
/*
** Generate reaction pattern by digitizing experimental interaction pattern
** comprising selected marker alleles
*/
    ReactionPattern = GenerateRecipientGenotype(ExpIntPattern, Thresholds);
/*
** Assign Haplotypes by computing all biallelic combinations of known or
** possible alleles; reaction patterns of such alleles with the probes in the
** selected set are stored ** in a HitTable; return a pointer to a list of all
** compatible alleles or haplotypes
*/
    AssignAlleles(AlleleArray1, AlleleAray2, ReactionStr, HitTable);
/*
** Apply string matching (optionally with weighted distance function) to
select ** all compatible donors
*/
    SelectCompatibleDonors(DonorRegistry, RecipientHaplotypes);
}
```

TABLE 1

HEA-panel composition showing blood groups and associated SNPs

| Blood Group | Phenotype | Polymorphism |
|---|---|---|
| Colton | $Co^a/Co^b$ | 134 C > T |
| Diego | $Di^b/Di^a$ | 2561 C > T |
| Duffy | $Fy^a/Fy^b$ | 125 G > A |
| | $Fy^x$ [Fy(b+$^w$)] | 265 C > T |
| | GATA (Fy(a−b−) | −33 T > C |
| Dombrock | $Do^a/Do^b$ | 378 C > T |
| | | 624 T > C |
| | | 793 A > G |
| | Hy+/Hy− | 323 G > T |
| | Jo(a+)/Jo(a−) | 350 C > T |
| Kidd | $Jk^a/Jk^b$ | 838 G > A |
| Kell | K/k | 698 T > C |
| Landsteiner-Wiener | $LW^a/LW^b$ | 308 A > G |
| Lutheran | $Lu^a/Lu^b$ | 230 A > G |
| MNS | GYPA (M/N) | 59 C > T |
| | GYPB (S/s) | 143 T > C |
| Scianna | Sc1/Sc2 | 169 G > A |
| Rh | S68N (C/c) | 203 A > G |
| Rh | A226P (E/e) | 676 G > C |
| Hemoglobin S | HbS | 173 A > T |

TABLE 2

Rh-panel composition showing AA change and associated SNPs

| Exon | Amino acid change | Polymorphism |
|---|---|---|
| 1 | W16C | 48 G > C |
| 2 | L60I | 178 C > A |
| 2 | S68N | 203 A > G |
| 2 | P103S | 307 C > T |
| 3 | N152T | 455 A > C |
| 4 | | 37 bp dup.-ins.* |
| 5 | F223V | 667 T > G |
| 5 | A226P | 676 G > C |
| 5 | E233Q | 697 G > C |
| 5 | L245V | 733 G > C |
| 7 | G336C | 1006 G > T |

*known as "pseudoD"

In the sequence listings attached, for the various exons 1, 2, 3, 5 or 7, the primer sequence of the forward and/or reverse primer (as indicated) is indicated with a "check" mark on the sequence listing, and the sequence of the other primer in the set (forward or reverse, as applicable) is shown in Table 3, as follows:

TABLE 3

| | |
|---|---|
| Exon 1: reverse primer: Rh CE<br>5' GCT ATT TGC TCC TTT GAC CAC 3' | (SEQ ID NO.:1) |
| Exon 2: forward primer RhD:<br>TCT CCC CAC AGA GCA GTT | (SEQ ID NO.:2) |
| Exon 3: reverse primer Rh CE:<br>CCT CAA GTG ATC TGC CTT CCT CAG | (SEQ ID NO.:3) |
| Exon 5: reverse primer Rh CE:<br>TGC TCA CCA TTC TGA TCT TCC T | (SEQ ID NO.:4) |
| Exon 7: reverse primer Rh CE:<br>CAT CTC CGT CAG GCA CTC CAT | (SEQ ID NO.:5) |

A number of other markers and alleles may also be assayed using the methods described herein, including HpA.

Dombrock: Two New Alleles—By probing five common mutations at positions Do-793, Do-624, Do-378, Do-350 and Do-323, using, for example, RFLP analysis, four alleles have been identified to date (Table 4):

TABLE 4

| | DO-793 | DO-624 | DO-378 | DO-350 | DO-323 |
|---|---|---|---|---|---|
| DoA | A | A | A | A | A |
| DoB | B | B | B | A | A |
| Hy | B | B | A | A | B |
| Jo | A | A | B | B | A |

BeadChip eMAP Design—In accordance with the format of elongation-mediated multiplexed analysis of polymorphisms (eMAP), pairs of encoded elongation probes were designed to interrogate the target at the five designated positions, selecting, in each pair, one probe matching the expected normal ("wild type") and a second probe differing from the first at or near the 3' terminus and matching the anticipated variant. Primers are used to generate amplicons serving as target sequences for subsequent elongation analysis, where the amplicons either include subsequences corresponding or complementary to the subsequences at, and proximal to the designated polymorphic sites, or which correspond or are complementary in whole to such subsequences. In the alternative, it is possible to generate sufficient concentration of the genomic DNA in the sample without amplification to allow their targeting, hybridization and elongation, using complementary probes and appropriate elongation conditions. An eMAP design incorporating in a single BeadChip probe pairs for all five mutations of interest, was used to analyze a subset of 63 samples, selected from a cohort of ~430 controls and clinical samples. The results are shown below in Table 5

TABLE 5

| DO-793 | DO-624 | DO-378 | DO-350 | DO-323 | | Cases | Freq |
|---|---|---|---|---|---|---|---|
| -1 | -1 | -1 | 1 | 1 | DoB/DoB | 14 | 0.22 |
| -1 | -1 | 0 | 1 | 0 | DoB/Hy | 17 | 0.27 |
| -1 | -1 | 0 | 1 | 1 | DoB/Sh | 3 | 0.05 |
| -1 | -1 | 1 | 1 | -1 | Hy/Hy | 1 | 0.02 |
| -1 | -1 | 1 | 1 | 0 | Hy/Sh | 1 | 0.02 |
| -1 | -1 | 1 | 1 | 1 | Sh/Sh | 0 | 0 |
| 0 | 0 | -1 | 0 | 1 | DoB/Jo | 2 | 0.03 |
| 0 | 0 | -1 | 1 | 1 | DoB/Ha | 5 | 0.08 |
| 0 | 0 | 0 | 1 | 1 | DoA/DoB | 11 | 0.17 |
| 0 | 0 | 0 | 1 | 1 | Hy/Ha | | |
| 0 | 0 | 0 | 1 | 1 | Ha/Sh | | |
| 0 | 0 | 0 | 0 | 1 | Jo/Sh | 0 | 0 |
| 0 | 0 | 0 | 0 | 0 | Hy/Jo | 0 | 0 |
| 0 | 0 | 1 | 1 | 0 | DoA/Hy | 1 | 0.02 |
| 0 | 0 | 1 | 1 | 1 | DoA/Sh | 0 | 0 |
| 1 | 1 | -1 | -1 | 1 | Jo/Jo | 0 | 0 |
| 1 | 1 | -1 | 0 | 1 | Jo/Ha | 0 | 0 |
| 1 | 1 | -1 | 1 | 1 | Ha/Ha | 0 | 0 |
| 1 | 1 | 0 | 0 | 1 | DoA/Jo | 5 | 0.08 |
| 1 | 1 | 0 | 1 | 1 | DoA/Ha | 2 | 0.03 |
| 1 | 1 | 1 | 1 | 1 | DoA/DoA | 1 | 0.02 |
| | | | | | | 63 | |

Four new allele combinations, highlighted in bold face font in Table 5 (DoB/Sh; Hy/Sh; DoB/Ha; DoA/Ha) are evident—wherein 1, 0 and −1 respectively denote allele combinations AA, AB or BA and BB.

TABLE 6

| | DO-793 | DO-624 | DO-378 | DO-350 | DO-323 |
|---|---|---|---|---|---|
| Ha | A | A | B | A | A |
| Sh | B | B | A | A | A |

These four combinations, which have been confirmed by sequencing of the corresponding amplicons, are readily shown to represent the combination of known alleles with two new alleles, namely (Table 6): That is, Ha differs from DoA, and Sh differs from DoB, by the replacement of, respectively, A by B and B by A in position Do-378. As a result, the combination of Ha and Sh generates the same string ("word"), namely 00011, as does the combination DoA/DoB; similarly, Hy/Ha also generates the same string. This degeneracy may account for the relatively high frequency of occurrence of that string, suggesting that observation of 000 in a first pass of analysis may be misattributed to the occurrence of DoA/DoB. However, the two 5-letter strings remain degenerate, and resolution of this ambiguity must invoke analysis of additional markers.

The six Dombrock alleles including the two new alleles identified herein generate the following 21 combinations.

TABLE 7

| | DoB | Hy | Sh | Jo | Ha | DoA |
|---|---|---|---|---|---|---|
| DoB | -1 -1 -1 1 1 | -1 -101 0 | -1 -1011 | 00 -1 01 | 00 -111 | 00011 |
| Hy | | -1 -111 -1 | -1 -1110 | 00 0 00 | 00 011 | 00110 |
| Sh | | | -1 -1111 | 00 0 01 | 00 011 | 00111 |
| Jo | | | | 11 -1 -11 | 11 -101 | 11001 |
| Ha | | | | | 11 -111 | 11011 |
| DoA | | | | | | 11111 |

As indicated in the Table 7, at the resolution provided by the first three Dombrock polymorphisms, namely DO-793, -624 and -378, several of the 3-letter allele combinations are degenerate. Complete resolution of the degeneracy of the allele combinations will require determination of polymorphisms beyond the current five.

Silencing Mutations: Duffy and GATA—The expression of an antigen can be affected by silencing mutations, for example in the GATA box of the gene encoding Duffy (Fy). Thus to establish allele combinations of the markers Fy 125 T>C and GA−33T>C, especially in the case of a heterozygous GA marker, may call for phasing, as described below.

Automated Allele Assignment: Hit Table—The process of selecting allele combinations which match or partially match a particular experimental pattern produced by eMAP preferably employs a hit table (such as Table 8 below) for the five Dombrock polymorphisms described above. Using the hit table in conjunction with a listing of known alleles, an algorithm of pattern matching can be applied to select, in automated fashion, matching or partially matching combinations of alleles which can be reviewed and edited in an integrated software environment such as that provided by the Automated Allele Assignment (AAA) program, described in U.S. application Ser. No. 10/909,638, incorporated by reference. In Table 8, "8" denotes a positive assay signal, indicating, for example, probe elongation, and "1" denotes a negative assay signal, indicating, for example, lack of probe elongation.

TABLE 8

| HIT TABLE | N | V | N | V | N | V | N | V | N | V |
|---|---|---|---|---|---|---|---|---|---|---|
| DoA | 8 | 1 | 8 | 1 | 8 | 1 | 8 | 1 | 8 | 1 |
| DoB | 1 | 8 | 1 | 8 | 1 | 8 | 8 | 1 | 8 | 1 |
| Hy | 1 | 8 | 1 | 8 | 8 | 1 | 8 | 1 | 1 | 8 |
| Jo | 8 | 1 | 8 | 1 | 1 | 8 | 1 | 8 | 8 | 1 |
| Ha | 8 | 1 | 8 | 1 | 1 | 8 | 8 | 1 | 8 | 1 |
| Sh | 1 | 8 | 1 | 8 | 8 | 1 | 8 | 1 | 8 | 1 |

TABLE 8-continued

RULES 8 == matched, 1 == mismatched
8 OR 8 = 8, 1 OR 1 = 1, 8 OR 1 = 1, 1 OR 8 = 8
Example DoB/Sh

| Reaction Pattern | 1 | 8 | 1 | 8 | 8 | 8 | 8 | 1 | 8 | 1 |
|---|---|---|---|---|---|---|---|---|---|---|
| Allele Combination | −1 | | −1 | | 0 | | 1 | | 1 | |

Haplotype Determination with Phasing—One method of distinguishing haplotypes (combinations of alleles on the same homolog) is to use phasing, as disclosed in U.S. application Ser. No. 10/271,602; International Application No. WO03034029(incorporated by reference). Phasing involves generating an elongation product from a probe capable of detecting a first polymorphic target site, and then determining if counterparts of other designated polymorphic sites are present within that elongation product. If so, this indicates that the two markers including both the first and the other designated polymorphic sites belong to the same allele.

More particularly, phasing is carried out by using encoded beads displaying elongation probes, which thereby identify both the probes and elongation products, and then annealing to the elongation product labeled oligonucleotide probes to determine whether or not counterpart(s) of additional polymorphic sites are present within the elongation product. By interrogating elongation products generated from probes directed toward a series of successive designated polymorphic sites, the phase of the combination of alleles generating a reaction pattern can be determined.

It should be understood that the terms, expressions and examples hereinabove are exemplary only and not limiting, and that the invention is defined only in the claims which follow, and includes all equivalents of the subject matter of those claims.

The invention claimed is:

1. The primers for exons 1, 2, 3, 5 or 7 of variants of genes RhCE and RhD, having the following sequences:

Exon 1: reverse primer: Rh CE           (SEQ ID NO.: 1)
5' GCT ATT TGC TCC TTT GAC CAC 3'

Exon 2: forward primer RhD:             (SEQ ID NO.: 2)
TCT CCC CAC AGA GCA GTT

Exon 3: reverse primer Rh CE:           (SEQ ID NO.: 3)
CCT CAA GTG ATC TGC CTT CCT CAG Exon 5: reverse primer Rh CE:           (SEQ ID NO.: 4)
TGC TCA CCA TTC TGA TCT TCC T Exon 7: reverse primer Rh CE:           (SEQ ID NO.: 5)
CAT CTC CGT CAG GCA CTC CAT.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gctatttgct cctttgacca c                                    21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tctccccaca gagcagtt                                        18

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcaagtga tctgccttcc tcag                                          24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgctcaccat tctgatcttc ct                                            22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catctccgtc aggcactcca t                                             21
```